United States Patent [19]

Zemel

[11] 4,103,227
[45] Jul. 25, 1978

[54] ION-CONTROLLED DIODE

[75] Inventor: Jay N. Zemel, Jenkintown, Pa.

[73] Assignee: University of Pennsylvania, Philadelphia, Pa.

[21] Appl. No.: 781,474

[22] Filed: Mar. 25, 1977

[51] Int. Cl.² ........................................... G01R 27/02
[52] U.S. Cl. ............................... 324/65 R; 23/254 E; 73/23; 324/71 R; 324/71 SN; 340/627
[58] Field of Search ................... 73/23, 27 R; 338/34; 324/65 R, 65 P, 32, 72, 71 SN, 71 R; 340/237 R; 23/254 E, 255 E

[56] References Cited

U.S. PATENT DOCUMENTS

| 2,711,511 | 6/1955 | Pietenpol | 324/71 SN |
| 3,295,022 | 12/1966 | Schelisch | 324/72 UX |
| 3,428,892 | 2/1969 | Meinhard | 324/71 SN |
| 3,831,432 | 8/1974 | Cox | 73/23 |

Primary Examiner—Stanley T. Krawczewicz
Attorney, Agent, or Firm—Holman and Stern

[57] ABSTRACT

Disclosed is an ion-controlled device for providing an electrical indication of a specific ion concentration in a fluid. An ion-sensitive membrane is placed over the junction of a gate controlled diode whose impedance is being measured. An external reference electrode is biased such that an inversion layer forms in the semiconductor material near the ion-sensitive membrane. Changes in the concentration of the unknown ion in fluid passing over the ion-sensitive membrane will affect the inversion layer in the gate controlled diode. The change in inversion layer will result in measurable changes in the diodes impedance.

12 Claims, 6 Drawing Figures

ION-CONTROLLED DIODE

BACKGROUND OF THE INVENTION

The present invention is related to ion-sensitive electrodes which provide an electrically measurable sensor for determining ion concentration in fluids.

Generally, ion-sensitive electrodes depend upon a particular ion in a fluid interacting with a membrane to modify the electrical characteristics of a measuring electrode. In recent years, the ion-sensitive field effect transistor (ISFET) has been drawing increasing interest from the scientific and technological community. One example of the ISFET is taught in U.S. Pat. No. 3,831,432 and herein incorporated by reference. These have numerous advantages stemming from their small size and the fact that they are truly semiconductor devices.

However, there are difficulties with the field effect transistor in that the source-drain biasing potential, no matter how small, will polarize the ionic solution in the vicinity of the source-drain electrodes. The effect of this polarization by the unscreened field is considered by many to produce slow drifts in the output which impairs the long-term stability in the field effect transistor. If an alternating current signal is used, to prevent slow drifts, the large Miller capacitance of the overlap region of the channel in the Field Effect Transistor will cause shunting of the signal through the ionic solution. The least effect of this shunting through the ionic solution is to change the response to the ion concentration in the vicinity of the ion-sensitive membrane resulting in inaccurate indication of the ion concentration in the fluid.

Additionally, the ISFET is not suitable for multiple ion sensing due to the complexity of connections which must be made to the ISFET associated with each different ion sensor. This complexity results in making the incorporation of the ISFET into integrated circuits more difficult and expensive.

Accordingly, an object of the present invention is to provide an ion-controlled diode (ICD) in order to measure, without adversely affecting, the ion concentration of fluids.

A further object of the present invention is to provide an ion-controlled diode which is capable of providing an analog or a digital output indicative of ion concentration, rendering it more compatible with integrated circuit technology.

It is a further object of the present invention to eliminate the polarization of an ionic solution, whose ion concentration is to be measured, by the measuring device itself.

A still further object of the present invention is to provide a high degree of isolation between the ion sensor region and the electronic sensing circuitry in an ion measurement device.

BRIEF SUMMARY OF THE INVENTION

According to the present invention, the foregoing and other objects are attained by providing a semiconductor-junction, separated from the fluid whose ion concentration is to be measured by an ion-sensitive membrane, and electrically connected to an impedance measuring apparatus. A reference electrode is provided in the ionic fluid and is biased at a potential causing an inversion region in the semiconductor material adjacent the surface of the ion-sensitive membrane. Changes in the polarization caused by ion exchange at the fluid/ion-sensitive membrane interface will change the charge density of the inversion layer and affect the admittance of the P/N junction. This admittance change is utilized either by an oscillator circuit to change oscillation frequency (and through a counter circuit providing a digital readout) or by an impedance measuring circuit (for an analog output) for indicating the ion concentration in the unknown fluid.

BRIEF DESCRIPTION OF THE DRAWINGS

A more complete appreciation of the invention and the attendant advantages thereof will be more clearly understood by reference to the drawings wherein.

DETAILED DESCRIPTION OF A PREFERRED EMBODIMENT

Figure 1:
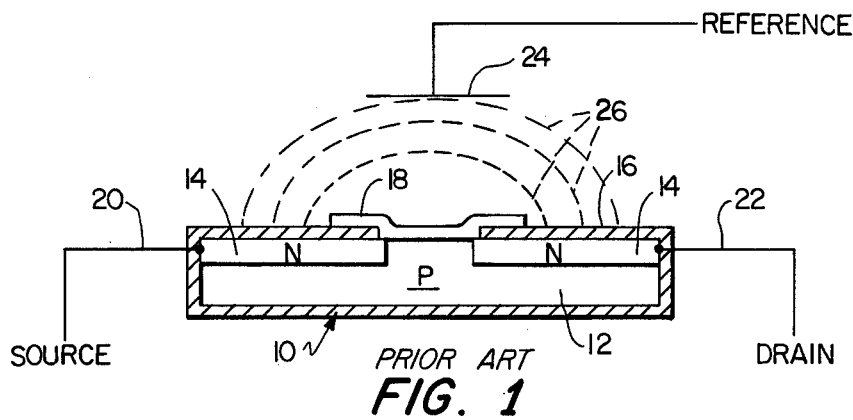
FIG. 1 is a cross sectional view of a typical prior art ion-sensitive field effect transistor (ISFET)

FIG. 1 teaches a typical ion-sensitive field effect transistor (ISFET) as known in the prior art. A field effect transistor 10 is comprised of P-type semiconductor material 12 and two distinct regions of N-type material 14. An insulator coating 16 surrounds the field effect transistor 10 with the exception of the area of the N—P—N junction. An ion-sensitive membrane (ISM) 18 is sealed to the oxide coating and covers the portion of the N—P—N junction left uncovered by the insulating coating 16.

A source connection 20 and a drain connection 22 make electrical contact with the two portions of N-type material 14. A reference electrode 24 is generally placed in the fluid some distance away from the ion-sensitive membrane 18.

In normal operation the source-drain biasing potential will produce a fringing field 26 as indicated in FIG. 1. The effect of this field is to polarize the ionic solution in the vicinity of the ISM 18 causing an abnormal ion concentration adjacent the ISM. The problems associated with this effect have been previously noted.

Figure 2:
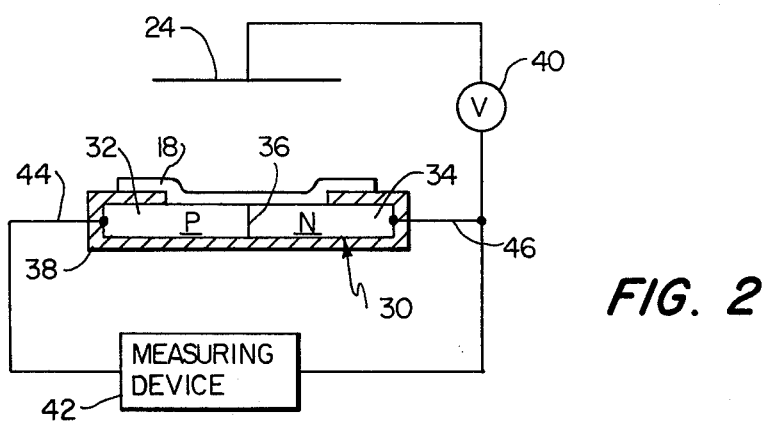
FIG. 2 is a cross sectional schematic view of the present invention.

The applicant's invention is schematically represented in FIG. 2 wherein a conventional gate controlled diode is schematically represented at 30. The diode is made up of P-type semiconductor material 32 and N-type material 34 forming a semiconductor junction 36. The diode is surrounded by an insulator material, in a preferred embodiment silicon oxide or nitride coating 38. The portion of the diode surface which is adjacent the P/N junction 36 is covered with the ion-sensitive membrane 18 as in the prior art. A conventional reference electrode 24 is connected to one of the semiconductor materials, in this instance N-type material 34 through a biasing supply 40. This biasing supply provides a means for converting any charge exchange polarization of the ion-sensitive membrane into a change in the strength of the inversion layer on the semiconductor material. P-type material 32 and N-type material 34 are connected to a measuring device 42 through electrode connections 44 and 46, respectively.

Measuring device 42 biases the diode at a convenient operating point although such bias is not essential for operation. Biasing supply 40 establishes a potential difference between reference electrode 24 and the diode. Because of this potential, an inversion layer is formed at the junction region of the diode. Increasing the potential of the biasing supply 40 results in a stronger inversion layer. It will be noted that the strength of an inversion layer on the diode effectively decreases the transit time of carriers in the inversion layer of the P/N junction 36. This change in transit time of carriers in the inversion layer of the P/N junction can be sensed by the measuring device as a change in the diode's capacitance or impedance at a high frequency. It is the change in the transit time due to the changes in the inversion layer which are responsible for changes in the electrical output which is measured by the measuring device 42.

The presence of the ion-sensitive membrane is such that, depending on the ion concentration of the fluid adjacent said membrane, the membrane will become polarized to a certain degree. The polarization of the membrane will cause the inversion layer in the diode to change in conductivity, thus affecting the transit time limited capacitance of the P/N junction. Therefore, changes in the polarization of the ion-sensitive membrane result in changes in the diode's capacitance (impedance) which changes are measurable by said measuring device 42.

The fact that the diode is biased to form an inversion layer eliminates the fringing fields 26 present in the prior art ISFET. The formation of the inversion layer by biasing the diode with respect to the reference electrode allows the change in inversion layer transit time and thus capacitance of the diode to reflect (through the ion-sensitive membrane) the ion concentration in the fluid to be measured. This electrical change then eliminates the necessity of having current flow through the diode as is required by the prior art ISFET and has the advantage of eliminating the fringing fields.

Figure 3:
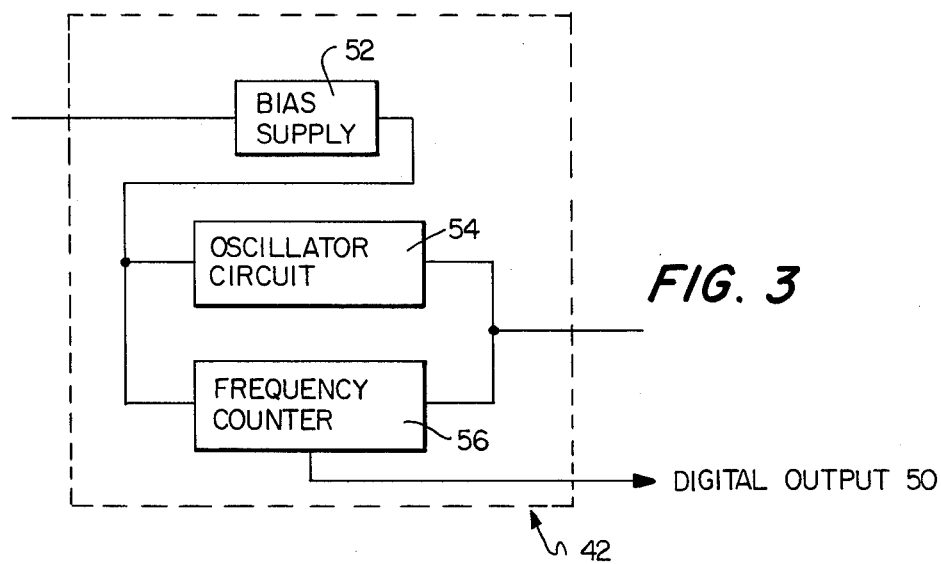
FIG. 3 is a block diagram of a preferred embodiment of a portion of FIG. 2.

FIG. 3 illustrates one embodiment of the measuring device 42 which would provide a digital output 50. Bia supply 52 would maintain the diode in back or forward bias while oscillator circuit 54 incorporates the diode's capacitance to produce an output frequency which varies in accordance with the capacitance of the diode. As the polarization of the ion-sensitive membrane changes, the admittance of the total P/N junction will change and thus the capacitance of the diode will be affected. Periodically, the frequency of oscillation is counted by frequency counter 56 which provides a digital output 50. Bias supplies, oscillator circuits, and frequency counters are well known and can be readily connected, as shown in FIG. 3, by one of ordinary skill in the art.

Figure 4:
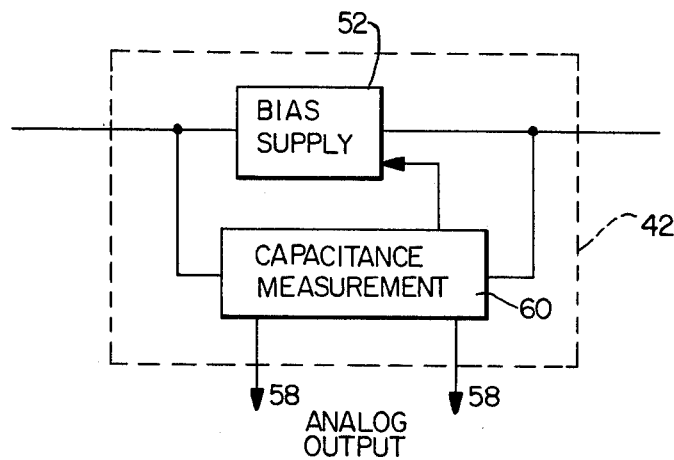
FIG. 4 is a block diagram of a further preferred embodiment of a portion of FIG. 2.

Similarly, an analog output 58 is possible as illustrated in FIG. 4. Changes in the bias supply to the P/N junction will change the admittance of the P/N junction and thus its capacitance. In FIG. 4 a capacitance measurement device 60 samples the capacitance of the P/N junction and adjust the bias supply to maintain a specific capacitance level. Thus, there will be changes in the bias voltage which are directly usable as an analog output 58. Again, bias supply circuits, which are responsive to capacitance changes, are known to those of ordinary skill in the art.

Figure 5:
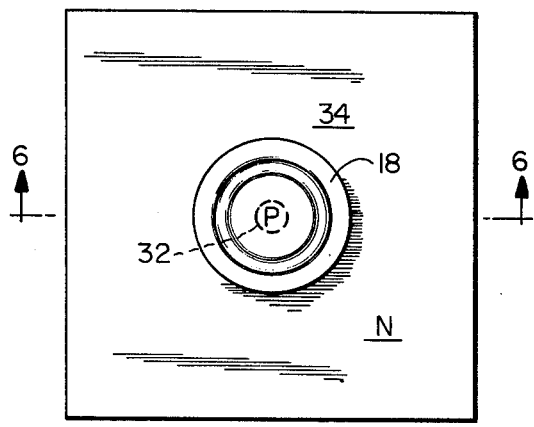
FIG. 5 is a plan view of a preferred embodiment of the present invention.
Figure 6:
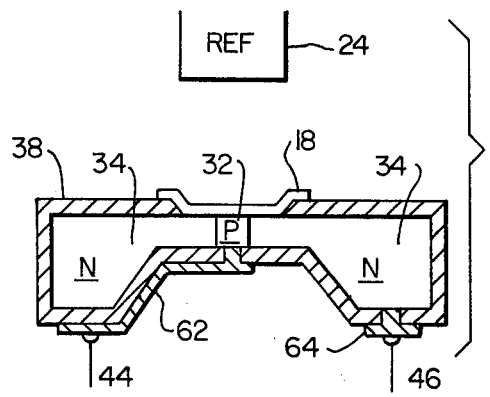
FIG. 6 is a cross sectional view of the embodiment of FIG. 5 along section lines 6—6.

FIGS. 5 and 6 illustrate a preferred embodiment of the diode which is particularly sensitive to changes in the inversion layer. The structure is essentially identical to the simplified version depicted in FIG. 2, although there is one additional benefit. Electrode connections 44 and 46 are made with metalized through-the-back connections 62 and 64 with the P-type and N-type material, respectively. The use of this type of connection with the ion-sensitive diode, protects the electrodes from exposure to the fluid whose ion concentration is to be measured. This type of connection in combination with the ion controlled diode has the advantage that it facilitates printed circuit and chip connections with the possibility that whole amplifier and microprocessor circuits can be provided on the unexposed side of the ion controlled diode (the side not containing the ion-sensitive membrane 18). It can be seen that the construction represented in the cross sectional view of FIG. 4 will provide a much larger P/N junction area than the simplified drawing in FIG. 2 while at the same time providing a relatively compact ion sensor construction.

Any of a wide variety of ion-sensitive membranes can be used in combination with the diode structure disclosed herein. The ion-sensitive membrane will be of the general class of ion selective materials that respond to one particular ion with minimum response to other types of ions.

Because of the simplicity of the ion controlled diode, the number of contacts are reduced below those necessary for the ISFET. This allows incorporation of multiple ion sensing configurations having different and distinct ion-sensitive membranes which are responsive to varying ions. The lack of fringing fields reduces the possibility of interaction between multiple sensors. Additionally, the logic or microprocessor circuitry can be built into the backside of the ion controlled diode providing an extremely compact and yet sensitive ion sensing device. It is noted that numerous combinations of electronic circuitry can be utilized to measure the capacitance (impedance) of the ion controlled diode and many more will become obvious to those of ordinary skill in the art based upon the above teachings. Examples given in FIGS. 3 and 4 are merely methods of providing a digital output or an analog output depending on the processing circuitry which will ultimately use the ion concentration information. In view of the numerous possibilities and applications for the ion controlled diode, obvious to those of ordinary skill in light of the above teachings, the scope of the patent is limited only by the claims appended hereto.

In the claims:

1. An ion sensor for sensing the presence and/or concentration of an ion in a fluid, said sensor comprising:
   an insulated semiconductor diode having a P/N junction; and
   an ion-sensitive membrane, separating said junction from said fluid and juxtaposed with said junction.

2. A chemical sensor, in combination with a means for measuring impedance of a semiconductor junction and a means for redistributing charges between a semiconductor diode and a membrane, for measuring the presence and concentration of a desired ion in a fluid, said sensor comprising:
   semiconductor diode means, having an inversion layer, for varying impedance in response to changes in said inversion layer; and
   membrane means, separating said diode means from said fluid, for changing the inversion layer in said diode means in response to changes in said desired ion concentration.

3. The sensor of claim 2 wherein said diode means includes N-type and P-type semiconductor material and comprises:
- a generally planar portion of one type semiconductor material having an upper and lower surface;
- a cylindrical insert of said other type semiconductor material in said planar portion forming a cylindrical P/N junction; and
- an insulative coating means, in combination with said membrane means, for sealing said semiconductor material from said fluid.

4. The sensor of claim 3 wherein said membrane means is located on said upper surface between said P/N junction and said fluid, and electrical contacts, connecting said N-type and P-type semiconductor materials with said means for measuring, are located on said lower surface.

5. The chemical sensor of claim 2 wherein said semiconductor diode means includes through-the-back connector means isolated from said fluid and responsive to said diode means, for making electrical contact with said semiconductor diode means.

6. A chemical sensor for sensing the presence and/or concentration of a desired chemical ion in a fluid comprising:
- semiconductor diode means having an inversion layer;
- membrane means, responsive to said diode means and said fluid and adjacent to and separating said diode means from said fluid, for reducing said inversion layer in response to said ion;
- means, responsive to said diode means and said membrane means, for redistributing charges between said semiconductor diode means and said membrane means; and
- means, responsive to said diode means, for measuring the impedance change of said semiconductor diode means, said impedance change indicative of the presence and concentration of said ion in said fluid.

7. The chemical sensor of claim 6 wherein said means for measuring includes:
- output means, responsive to said diode means, for providing a digital indication of the presence and concentration of ion in said fluid.

8. The chemical sensor of claim 6 wherein said means for measuring includes:
- output means, responsive to said diode means, for providing an analog output indicative of the presence and concentration of said ion in said fluid.

9. The chemical sensor of claim 6 wherein said means for redistributing charges includes:
- a reference electrode in said fluid at some distance from said membrane means; and
- potential means, electrically connected between said reference electrode and said semiconductor diode means, for producing an inversion layer in said semiconductor diode means.

10. The chemical sensor of claim 7 wherein said output means comprises:
- bias means, responsive to said diode means, for maintaining said semiconductor diode means in a preferred bias mode;
- oscillator circuit means, responsive to said semiconductor diode means, for providing an output signal the frequency of which is a function of said inversion layer in said semiconductor diode means; and
- frequency counter means, responsive to the output of said oscillator circuit means, for providing a digital output indicative of the ion concentration in said fluid.

11. The chemical sensor of claim 8 wherein said semiconductor diode means has capacitance and said output means comprises:
- capacitance measurement means, responsive to said diode means, for providing a signal indicative of changes in said semiconductor diode means capacitance; and
- bias supply means for biasing said semiconductor diode means and, responsive to said signal from said capacitance measurement means, for adjusting the bias of said semiconductor diode means to maintain a constant capacitance therein, said bias supply coincidentally providing an analog output indicative of the presence and/or ion concentration in said fluid.

12. The chemical sensor of claim 6 wherein said sensor further includes through-the-back connector means, isolated from said fluid, and responsive to said diode means, for making electrical contact with said semiconductor diode means.

* * * * *